United States Patent [19]

Hensley et al.

[11] Patent Number: 4,557,142
[45] Date of Patent: Dec. 10, 1985

[54] APPARATUS AND METHOD FOR REAL-TIME MEASUREMENT OF DRILLING FLUID PROPERTIES

[75] Inventors: Gary L. Hensley, Houston; Jan Van Dokkum, Crosby, both of Tex.; Adrianus Groeneweg, Dordrecht; Gerritt Stolk, Lage Swaluwe, both of Netherlands

[73] Assignee: Hutchinson-Hayes International, Inc., Channelview, Tex.

[21] Appl. No.: 541,725

[22] Filed: Oct. 13, 1983

[51] Int. Cl.$^4$ .............................................. E21B 47/00
[52] U.S. Cl. .......................................... 73/153; 73/60
[58] Field of Search ..................... 73/153, 433, 60, 434

[56] References Cited

U.S. PATENT DOCUMENTS

| | | | |
|---|---|---|---|
| 2,252,014 | 8/1941 | Lupfer | 73/153 X |
| 2,977,790 | 4/1961 | Dubsky et al. | 73/60 |
| 3,147,616 | 9/1964 | Rome | 177/208 X |
| 3,436,968 | 4/1969 | Unger et al. | 73/433 |
| 3,503,267 | 3/1970 | Shiba et al. | 73/434 |
| 3,899,926 | 8/1975 | Haden | 73/153 |

Primary Examiner—Jerry W. Myracle
Attorney, Agent, or Firm—Bill B. Berryhill

[57] ABSTRACT

A system for real-time measurement of multiple properties of drilling fluids from a single sampling point may comprise: a pump for transferring fluids in the system, the suction of which may be alternately communicated through suction conduits with a reservoir of drilling fluids being measured and the source of cleaning fluids; valves connected in the suction conduits for alternately allowing or preventing fluid communication between the pump and the drilling fluid reservoir or the source of cleaning fluids; a weight measuring device connected to the discharge side of the pump for receiving and measuring the weight of drilling fluids therefrom; and a viscosity measuring device connected to the discharge of the pump for receiving and measuring indices of viscosity of the drilling fluids therefrom. A source of power is connected to the pump, the weight measuring device, the viscosity measuring device and control apparatus. The control apparatus is also connected to the pump, the weight measuring device and the viscosity measuring device for controlling the operation thereof.

40 Claims, 5 Drawing Figures

APPARATUS AND METHOD FOR REAL-TIME MEASUREMENT OF DRILLING FLUID PROPERTIES

BACKGROUND OF THE INVENTION

1. Field of the Invention

The present invention pertains to methods and apparatus for determining the properties of drilling fluids. Specifically, the present invention pertains to methods and apparatus for real-time measurement and stored data acquisition, evaluation and indication of multiple properties of drilling fluids such as mud temperature, mud weight and API indices of viscosity, i.e. plastic viscosity, yield point, ten-second gel strength, ten-minute gel strength.

2. Brief Description of the Prior Art

Drilling fluids are introduced into the hole of a well during drilling for a number of reasons. One of the main reasons is to prevent loss of control of the well when encountering high pressure gas or other fluid containing formations by maintaining a static pressure head thereon. Drilling fluids also help to maintain a clean hole, protect formations through which the drill string passes, lubricate the drill bit and reduce the friction associated with turning the drill string, etc. Of course, the properties of the drilling fluids are important in considering the effectiveness of the drilling fluids are these uses.

Drilling fluids or "drilling muds" are colloidal suspensions having two parts: a liquid phase and a solid phase. Depending upon the type of fluid, the liquid phase can also have two parts: a continuous phase and a dispersed phase. In the majority of drilling fluids, the continuous phase is water. However, some water-based fluids containing diesel oil will form emulsions of oil droplets (the dispersed phase) surrounded by water (the continuous phase). Muds with a continuous oil phase and a dispersed water phase are called invert emulsions and are classed as oil-based muds along with those fluids without any significant water content.

The solid phase of all drilling fluids consists of commercial and drilled solids. Commercial solids are solids added to the drilling fluids to achieve certain properties. The most commonly employed commercial solids include bentonite, barite, and various thinners. Drill solids are solids that enter the drilling fluids from the well formation in the form of cuttings or carvings.

Rheology has been defined as the science of the flow and deformation of matter. It is important to know the rheological properties of drilling fluids to ensure that optimum properties are maintained for performing their functions. Rheological measurements aid in the diagnosis and treatment of various drilling fluids for related problems encountered during drilling.

The rheology of a drilling fluid includes the measurement of its temperature, weight, and viscosity. The temperature and weight of a drilling fluid appear to be relatively easy to determine. However, the presently used methods, particularly for determining weight, are relatively primitive. The equipment for doing so is usually a mud balance having a balanced beam at one end of which is a mud cup and the other end of which is a fixed counterweight. A rider weight is free to move along a graduated scale on the beam. The cup is filled with mud or drilling fluid to be tested and balanced by moving the rider weight along the graduated scale. One of the problems associated with such measurements is that the mud samples are not always taken from the same location in a mud or drilling fluid tank. Generally, the drilling fluid is heavier toward the bottom of the tank because of the precipitation of solids therein. Thus, different readings can be obtained depending on how far below the surface of the fluid the sample is taken. Furthermore, such sampling is largely by hand and the time from taking the sample until determining mud weight can vary substantially. Thus, this method does not give a real-time measurement or provide for stored data acquisition, evaluation and indication of the multiple properties of drilling fluids. There are other methods of measuring the properties of drilling fluids, i.e. with gamma ray devices and differential pressure devices. However, such methods are relatively expensive and not extremely accurate.

Another rheological property of drilling fluids is viscosity. Viscosity is defined as the internal resistance of a fluid to flow due to an applied force. When a fluid does flow, the internal resistance or force tends to oppose the flow. This internal force is called the shear stress. The internal force can be thought of as a frictional force resulting from one "layer" of fluid as it slides past another. The rate at which these "layers" of fluid within the drilling fluid move past each other is called the shear rate. The ratio of shear stress to shear rate is called the viscosity of the fluid and may be expressed by the formula:

$$\text{viscosity} = \frac{\text{shear stress}}{\text{shear rate}}$$

Drilling fluids can be categorized into two general types primarily based on the viscosity of the fluid: Newtonian fluids (constant viscosity); Non-Newtonian fluids (variable viscosity). The Newtonian fluids are the simplest types of fluids. The shear rate is directly proportional to the shear stress with this type of fluid. Water and many oils are Newtonian fluids. Since viscosity is the ratio of shear stress to shear rate, this means that a plot of shear stress to shear rate would result in a straight line running through the origin. Therefore, for any point along this plot, the shear stress divided by the shear rate will result in the same number.

Non-Newtonian fluids, of which drilling fluids are typical, do not exhibit the direct proportionality between shear stress and shear rate that Newtonian fluids do. The ratio is between shear stress and shear rate is not constant, but is dependent upon the shear rate. Since this ratio is not constant but varies with the shear rate, ratio between shear stress and shear rate is called the apparent viscosity. Thus, a Non-Newtonian fluid is not described by a single viscosity term as with the Newtonian fluid.

Two types of Non-Newtonian fluids are Bingham Plastic fluids and Pseudoplastic fluids. When shear stress is plotted versus shear rate for a Bingham Plastic fluid, a straight line results but does not pass through the origin. Where the line intercepts the ordinate in a plot of shear stress versus shear rate is defined as the yield point (YP). For a Pseudoplastic fluid, a plot of the shear stress versus shear rate has the shape of a curve rather than a straight line.

For a Bingham Plastic fluid, a finite amount of shear stress (y axis intercept) must be applied before fluid begins to flow. This quantity is defined as the yield point (YP). The slope of the line for the Bingham Plastic fluid is called the plastic viscosity (PV). In practical significance, plastic viscosity (PV) is a measurement of the internal resistance to flow due to the amount, type and size of the solids in the drilling fluid or mud. It is due to mechanical friction of the solids in the mud as they come in contact with each other and with the liquid phase of the mud. Solids present in the mud also influence the viscosity property known as the yield point. The yield point (YP) is a measure of the initial resistance to flow due to the electrostatic attractive forces located on or near the surface of particles. It is a dynamic measurement. The yield point is dependent on the type of solids present and their respective surface charges, the concentration of these solids, and the type and concentration of any other ions or salts that may be present.

In practice, as specified by the American Petroleum Institute (API), PV is expressed as the number of dynes per square centimeter of tangential shearing force in excess of the Bingham yield point (YP) that will induce a unit rate of shear. When using a direct reading viscometer, PV is found by subtracting a 300 rpm reading from a 600 rpm reading. Similarly, in practice the Bingham yield point (YP) is determined by subtracting the plastic viscosity (PV) from the 300 rpm reading.

Similar to the yield point (YP), gel strength is a measure of the ability of the mud to form a gel structure when it rests and then become fluid again once agitated. The gel strength is a measure of the stress required to break a gel structure under static (non-flow) conditions. It is also a measure of the same particle to particle forces that is determined by yield point (YP), except that the gel strength is measured under static conditions and the yield point is measured under dynamic conditions. The static conditions used in the measurement of gel strength are for ten seconds and ten minutes at rest.

As previously indicated, the plot of shear stress versus shear rate for a pseudoplastic fluid is a curve rather than a straight line. Mathematically, a pseudoplastic fluid can be expressed as:

$$SS = k(SR)^n$$

where
where $n < 1$ and:
SS = shear strength
SR = shear rate
n = flow behavior index
k = consistency index The k index is a measure of consistency. The larger the value of k, the more viscous is the fluid. On the other hand, n is the flow behavior index. It is a measure of the degree of non-Newtonian behavior of the fluid. When n equals 1, the fluid is Newtonian. The flow behavior index n is calculated from the equation:

$$n = 3.32 \log \frac{(\theta 600)}{(\theta 300)}$$

where:
n = flow behavior index
$\theta 600$ = dial reading at 600 rpm
$\theta 300$ = dial reading at 300 rpm Sometimes other dial readings are used to better represent actual mud flow in the annulus. For example, instead of 600 rpm and 300 rpm, dial readings taken from 200 rpm and 100 rpm are used. If such other shear rates are used, the higher sheer rate must be twice the lower shear rate, i.e. 200 rpm/100 rpm, 60 rpm/30 rpm. Once n is determined, the consistency index may be calculated. Unlike n, the k value contains specific units. The equation that is used to calculate k depends upon the units desired. For example, the most common equation used to calculate k is:

$$k = \frac{1.07 \times \theta 300}{511^n}$$

where:
k = consistency index in units lbs-sec$^n$/100 ft$^2$
n = flow behavior index
$\theta 300$ = dial reading at 300 rpm The most modern method of measuring viscosity utilizes direct indicating viscometers which are rotational type instruments powered by means of electrical motors or hand cranks. Mud is contained in an annular space between two cylinders. The outer cylinder or rotor sleeve is driven at a predetermined constant rotational velocity. The rotation of the rotor sleeve in the mud produces a torque in the inner cylinder or bob. A torsion spring restrains movement. A dial attached to the bob indicates displacement of the bob. Instrument constants are adjusted so that plastic viscosity PV and yield point YP (in the case of Bingham Plastic fluids) or flow behavior index n and consistency index k (in the case of pseudoplastic fluids) are obtained by using readings from the rotor sleeve speeds from 300 and 600 rpm.

There are several problems related to direct indicating viscometers. Of course, with hand crank instruments, rotational speeds are not always the same and the time between the measurements are not always accurate. The temperature of the fluid at the point of measurement may be considerably different than at the point of actual use. There are frictional forces in all these type instruments which can affect the readings thereof. Like in the weight measuring devices of the prior art, the samples placed in these types of instruments may come from different levels in the drilling fluid tank resulting in non-uniform measurements. As in any manual means of measurement, time at the point of measurement may vary considerably so that the measurements taken have no real-time correlation. Thus, it can be understood that the apparatus and methods for measuring the weight and viscosity of drilling fluids are, to say the least, primitive and somewhat less than accurate. Although the inaccuracies may not have been so important in the past, it is becoming more and more important since the cost of drilling fluids is a substantial portion of the total cost of drilling an oil and/or gas well. If the drilling fluids are not of the optimum properties, the cost may be extremely great and the degree of control of the well less than desired.

SUMMARY OF THE INVENTION

In the present invention a system is provided for real-time measurement and stored data acquisition, evaluation and indication of multiple properties of drilling fluids from a single sampling point. The system may include a pump for transferring fluids in the system and the suction of which may be alternately communicated through suction conduits with a reservoir of drilling fluid being measured and a source of cleaning fluids. Valves are connected in the suction conduits for alternately allowing or preventing fluid communication between the pump and the drilling fluid reservoir of the source of the cleaning fluids. The system includes a weight measuring device and a viscosity measuring device connected to the discharge side of the pump for receiving and measuring the weight and indices of viscosity, respectively, of the drilling fluids therefrom. A source of power is connected to the pump, valves, and the weight and viscosity measuring devices and controls are provided for controlling the operation of the same.

The weight measuring device and the viscosity measuring device of the present invention are unique in construction. Both include permanent magnetic assemblies for producing a constant magnetic field and a coil disposed in the magnetic field connected to the source of power and capable of producing a force directly proportional to the current applied thereto to counteract forces indicative of the particular property of the drilling fluid being measured.

The system of the present invention therefore permits immediately usable on-rig, real-time measurement of drilling mud weight and indices of viscosity which may incorporate computer aided display, manipulation and recall. Mud weight, plastic viscosity, yield point, gel strength and temperature of drilling fluids may be sampled at regular short intervals from a single sampling point. These readings may be immediately displayed at selected viewing points and also on a computer digital display nearby. Using an auxiliary computer, adjustments may be made in the drilling fluids by adding or reducing certain components to keep the drilling fluids as close as possible to optimum properties or characteristics. The system uses precise electronic techniques to obtain accurate and consistent data avoiding the introduction of error common to the methods and instruments now used to measure drilling fluid properties. By more accurate and timely information, the properties of the drilling fluid can be adjusted for optimum effect and may result in substantial savings in the cost of the drilling fluids program. Many other objects and advantages of the invention will be apparent from reading the description which follows in conjunction with the accompanying drawings.

DESCRIPTION OF PREFERRED EMBODIMENTS

Figure 1:
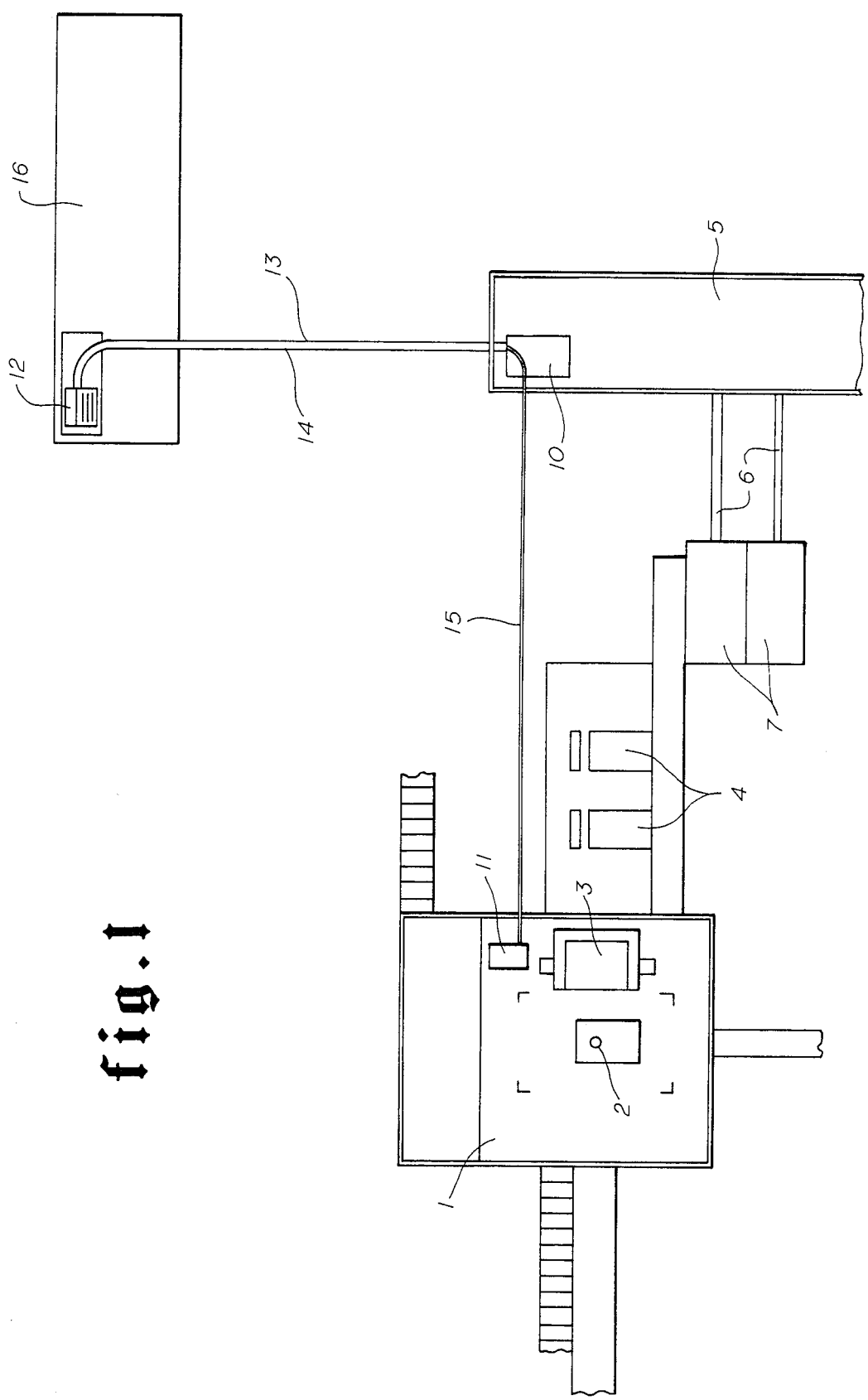
FIG. 1 is a partial plan view of a drilling rig illustrating placement of certain components of the present invention.

Referring first to FIG. 1, there is shown a drilling rig, the rig floor 1 of which is positioned over a well hole 2 being drilled for oil and/or gas. Illustrated on or near the rig floor 1 are drawworks 3 and engines 4 which supply power to the drilling rig. Near the rig is a mud tank or reservoir 5 which is connected by suction lines 6 to mud pumps 7. The mud pumps 7 supply drilling mud or fluids to the drilling rig for the purpose of maintaining control over the well hole, lubricating the drill string, etc.

Mud systems for drilling may include a number of components, e.g. shale shakers, desanders, desilters, etc. It is not the purpose of the present invention to describe such systems. For the purposes of the present invention, it is sufficient to know that drilling muds or fluids are relatively complex in composition, containing various liquids and solids for producing a drilling fluid of the desired properties. The final product or composition is uniformly mixed and eventually reaches a suction tank or reservoir such as the one 5 illustrated in FIG. 1. It is at this point that it is important to know the critical properties of the drilling fluid, i.e. temperature, weight, plastic viscosity, yield point, and gel strength. It is this purpose for which the system of the present invention was designed. The system is designed for on-rig, real-time measurement of these multiple properties of drilling fluids from a single sampling point, i.e. the suction tank 5. The term "real-time measurement" as used herein and in the claims which follow is defined as: on stream, instantaneous reading of information or characteristics that may be converted into information, taken, transmitted and indicated within the actual time framework during which a physical process happens within the context of the performance of computations of digital systems, the results of which guide a process.

The system of the present invention comprises three basic components: a pit transducer 10; annunciator 11, and computer processor 12. These components are connected by cable data links 13, 14 and 15. It will be noted that each of these basic components, pit transducer, 10 annunciator 11 and computer processor 12, are illustrated in insets of FIG. 1. The pit transducer 10 includes a temperature measuring device, a weight measuring device, a viscosity measuring device, a pump, interconnecting piping with electronically controlled valves, and an electronic control unit for providing the logic for normal operating cycles, cleaning cycles and signal outputs to other units. The pit transducer 10, an extremely important part of the system, will be described in more detail hereafter. For present purposes, it is sufficient to know that the pit transducer 10 takes samples from a single point in the mud reservoir 5 at predetermined intervals and measures the characteristics thereof. These measurements are transmitted to the computer processor 12 and annunciator 11 by the cable data links 13, 14 and 15.

The annunciator 11 may be located on the rig floor 1 so that the person in charge of drilling can have the measurements made by the pit transducer 10 immediately displayed to aid the driller in the drilling program. Alternately, the annunciator 11 may be located directly at the pit transducer 10. The annunciator 11 simply displays in digital form six items of data most recently collected from the pit transducer 10. These items of data may be displayed in rotation with a change in item occurring every few seconds. The item displayed is identified by a function number with legal key on the face of the readout.

The computer processor 12 is preferably located in a protected environment such as a trailer 16. It receives signals from the pit transducer 10 and stores data elements for recall and manipulation. Its digital display performs similarly to the annunciator display, showing in rotation the six items most recently collected. A built-in printer may provide a paper tape log in normally operating mode of readings every few minutes interrupting the cycle in recall mode to provide at least a twenty-four hour listing of items selected. This permits temperature adjustment of readings through computational means, recall of readings through fluid circulation to observe adjusted properties, transmission of data to remote locations for off-drill-site monitoring and analysis.

Referring to the schematic of FIG. 2 and the perspective of FIG. 3, the system of the present invention and particularly the pit transducer 10 will be described in more detail. All of the utility connections for the system are brought to the pit transducer 10 which includes connections for mud, a cleaning medium such as diesel fuel, air and electrical power. The pit transducer has a mud inlet 21, mud discharge 22, cleaner inlet 23 and cleaner discharge 24. It has an air inlet 25, electrical power connection 26 and electrical interface connection 27, by which electrical signals are transferred via cable data links between the pit transducer 10, the annunciator 11 and the computer processor 12. The electrical power connection 26 is connected to a source of electricity, e.g. 120 volt single phase, 60 cycle. The drilling rig air supply may be connected to the air inlet 25 and the system may be pressure-regulated to accept up to 125 psig. Air volume is minimal and does not exceed 1 SCFM.

Since the pit transducer 10 is located directly above the mud pit or suction tank 5, the mud inlet 21 may be connected simply by providing a hose extending into the mud pit or tank 5 at a fixed location and preferably includes a screened inlet to prohibit large particle blockage. Since fluid suction and transit are accomplished by a self-priming air diaphragm pump, no valving is required below the mud surface. After sampling, the mud is discharged from the mud discharge 22 to the mud tank or reservoir 5.

The cleaning fluid, e.g. diesel fuel or water, may be obtained from rig fuel supply which is connected to the cleaner inlet 23. Demand is minimal requiring approximately six gallons per cleaning cycle. The cleaning fluid may be discharged via the discharge 24 to the mud tank.

The pit transducer 10 includes a viscosity measuring device 32, a mud weight measuring device 33, a power center 34, control or logic center 35, fluid transit pump 36, and a temperature sensing device 37. The viscosity measuring device 32, weight measuring device 33 and temperature measuring device 37 are connected by electrical wiring 61, 62, 63, to the wireway 60 which provides interconnecting electrical conduits for connecting these items to the power center 34 and logic center 35. Mud inlet 21 and cleaning fluid inlet 23 are connected to the suction side of the pump 36 via air operated valves 44 and 46. The pump 36 is preferably a self-priming air-operated diaphragm pump, the discharge of which is connected to the viscosity measuring device and the mud weight measuring device 33. These units are in turn discharged through the mud discharge 22 and cleaner discharge 24 via air oprated valves 45 and 47. An air vent 28 is provided in the discharge outlet. The pump 36 is provided with an air discharge 31.

As previously mentioned, rig air is supplied to the pit transducer 10 at the air inlet 25. A filter 48 is provided for filtering the air and a pressure regulator 49 for reducing the air pressure. A low air pressure level shut down switch 50 and air oiler 51 may also be provided at the air inlet. Downstream of the air oiler 51 is an air manifold 65 which supplies air to five solenoid operated valves 38, 39, 40, 41, and 42. Air is supplied to the air operators of the valves 44, 46, 45 and 47 through solenoid valves 38, 39, 40 and 41, respectively, and to the air operated pump 36 through solenoid valve 42. The solenoid valves 38, 39, 40, 41 and 42 are electrically connected to the wireway 60 for interconnection to the power center 34 and logic or control center 35.

The power center 34 may include a multiple tap single phase transformer providing the necessary operating voltages for the various electrical, electronic and electromechanical devices of the system. The power center 34 may also include a voltage control and stabilization printed circuit board with rectifiers for direct current, stabilizing transistors, and diodes. An extruded aluminum heat sink may be provided for dissipation of thermal energy. A control relay printed circuit board may be installed in the power center 34 for the control and regulation of main relays and electromechanical solenoid valves.

The control or logic center 35 provides a series of electronic controls interfaced with the components of the pit transducer 10 to provide operation frequencies and commands and receive and translate output signals that may be analyzed and converted into usable data as to mud weight, temperature, yield point, plastic viscosity, ten second gel strength and ten minute gel strength. These controls include three major elements: timing sequence card, coil amplifier card and motor regulator card.

The timing sequence card provides signal pulse generator sections and divider sections for establishing timing references and establishing timing sequences to lengths suitable for the operation of the processes of the pit transducer 10 with a minimum of integrated circuits. A decoding section of this card designates the appropriate output amplifier circuits for command instructions.

The motor regulator card operates upon receipt of commands issued from the timing sequence card so as to supply motors with suitable voltage levels for given speeds. The speed is dictated by an analog voltage through potentiometer adjustments based on a reference voltage.

The coil amplifier card interfaces optical position indicators on the mud weight device and the viscosity device with measurement value converters that receive weight and viscosity signals passed through a current decoder. These are the bases of signals from which desired values are derived in remote readout and display circuitry.

Figure 4:
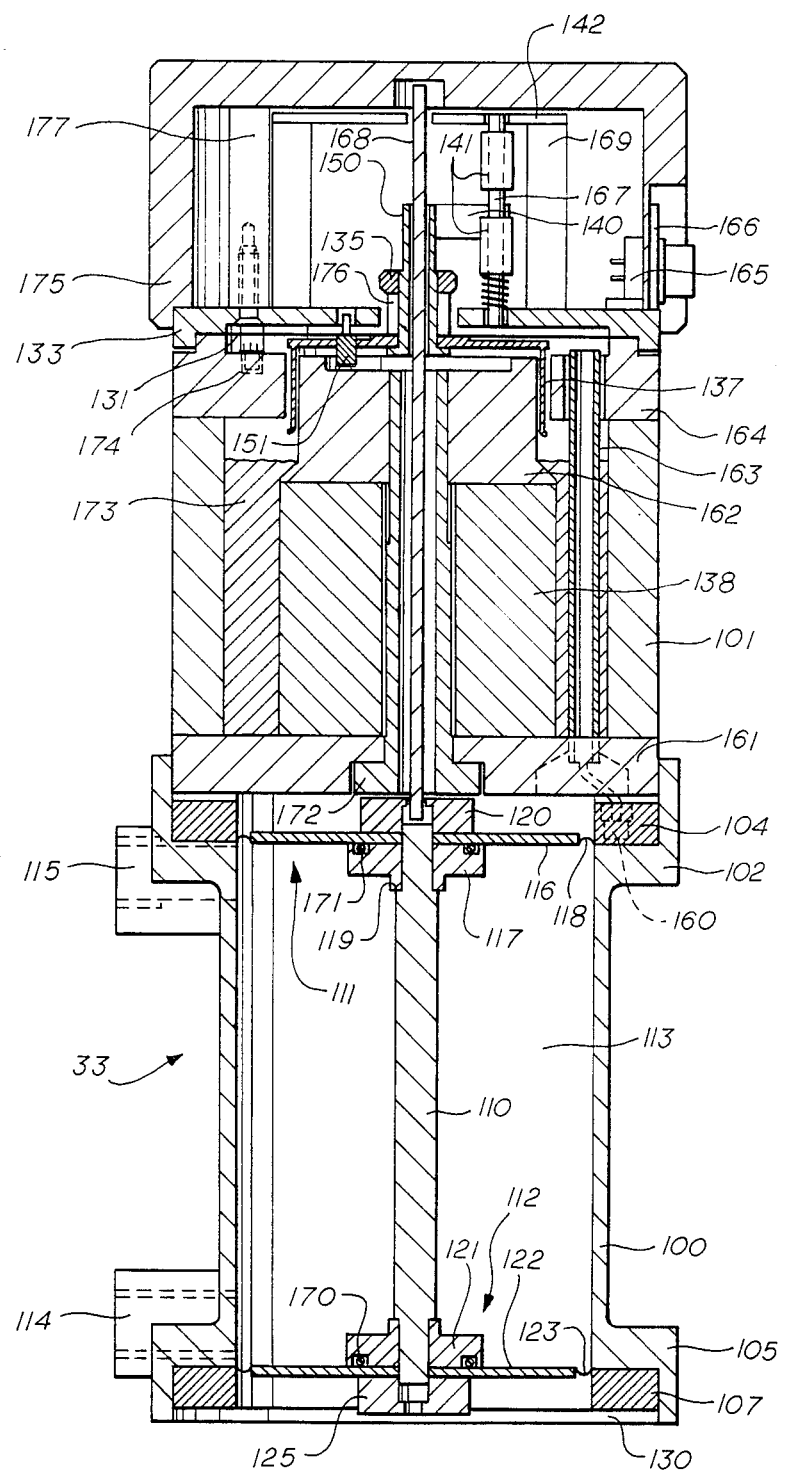
FIG. 4 is a sectional elevational view of a mud weight measuring device, according to a preferred embodiment of the invention.

The mud weight measuring device 33 of the present invention is a unique device and will now be described in greater detail with reference to FIG. 4. The purpose of the device is, as indicated, to obtain the weight of a fixed volume of drilling fluid. The mud weight device comprises a cylindrical fluid housing 100 surmounted on which is a magnetic housing 101. The cylindrical housing 100 may be provided with an upper radial flange 102 having holes (not shown) radially spaced therearound through which studs or bolts (not shown) may pass for threaded engagement with corresponding threaded holes in the magnetic housing 101. It will be noted that there is an intervening ring 104 between the flange 102 and the magnetic housing 101. The purpose of this ring 104 will be described in more detail hereafter. The lower portion of the cylinder 100 may also be provided with a radial flange 104 having holes (not shown) therethrough for receiving bolts (not shown) by which a ring 107 and bottom plate 130 are attached to the cylinder 100.

Centrally disposed in the cylindrical housing 100 is a central shaft 110 at the upper and lower ends of which are fixed concentric circular upper and lower plate assemblies 111, 112, which with the inside walls of the housing 100 define a fixed volume cylindrical chamber 113 for receiving fluids through an inlet 114 or from which fluids may be discharged through an outlet 115. The upper plate assembly 111 includes an upper plate 116 and a lower smaller diameter plate 117 between which is sandwiched a flexible diaphragm 118 and seal ring 171. The peripheral edges of the diaphragm 118 extend radially beyond the edges of the upper and lower plates 116 and 117 and are clamped between an upwardly facing surface of the radial flange 102 and a downwardly facing surface of the ring 104. The plate assembly 111 is fixed on the shaft 110 by retaining it between a stop shoulder 119 and a nut 120 threaded to the shaft 110. The nut 120 also acts as an upward stop.

In like manner, the lower plate assembly 112 comprises upper and lower plates 121 and 122 between which is sandwiched a flexible diaphragm 123 and seal ring 170. The peripheral edges of the diaphragm 123 are securely retained between a downwardly facing surface of the flange 105 and an upwardly facing surface of the ring 107. The lower plate assembly 112 is also fixed to the shaft 110 by a nut 125 threadedly attached thereto. The nut 125 acts as a downward stop.

Thus, it is seen that the diaphragms 118 and 123 provide sealing between the plate assemblies 111 and 112 and the cylindrical housing 100 while allowing limited vertical movement of the shaft 110 and plate assemblies 111 and 112 relative to the housing 100. It can also be understood that if the chamber 113 is filled with fluid through the inlet 114, a fixed volume of the fluid can be lifted or lowered by limited amounts without disturbing the volume therein.

Centrally disposed in the magnetic housing 101 is a permanent magnet 138 and an inside magnetic field 162 through the center of which is a central tubular stabilizer 172. A base plate 161 separates the components of the magnetic housing 101 from the components of the fluid housing 100. Plastic insulation material 173 may be poured in the annular space surrounding the permanent magnet 138 to insulate it from the housing 101. A wireway 163 may be placed through the insulation 173 for receiving a wire running from a temperature sensor 160 mounted in the ring 104. The purpose of the temperature sensor 160 is to determine the temperature of mud in the chamber 113.

At the upper end of the magnetic housing 101 is an outside magnetic field member 164. An annular space exists between the outside magnetic field 164 and inside magnetic field 162 creating a constant magnetic field therein. Freely disposed in this magnetic field is an annular coil 137 which is supported by a flat spring 131 to which it is attached by bushing 150, nut 135 and spacer 176. The flat spring 131 is retained at the upper end of the housing 101 by retaining ring 133. A temperature sensor 174 is provided to measure the temperature of flat spring 131.

Centrally disposed in the bushing 150 is a pull shaft 168 which extends through the central stabilizer 172 for threaded connection to the nut member 120. Movement of the pull shaft 168 upwardly or downwardly will effect upward movement of the shaft 110 and the fixed volume of fluid in the chamber 113.

Closing the upper portion of the mud weight measuring device 33 is a housing cap 175 which is held in place by cap mounting brackets 177. Also enclosed by the cap 175 is a spacer 169 and bracket 142. The bracket 142 and the retainer ring 133 support an optical device 141 for sensing the position of a vane 140 attached to the bushing 150. A spacer 167 separates components of the optical device 141. The optical device 141 is a commercially available device and in this application senses the vertical position of the pull shaft 168 and controls the current applied to coil 137 so that the coil lifts the pull shaft 168, and consequently the central shaft 110, upper and lower plate assemblies 111, 112 and fluids in chamber 113 to a predetermined elevation. The optical device 141 and coil 137 are interfaced with the electronics in the power center 34 and control the logic center 35 through electrical connection 165 attached to the cap 175 by electrical connector bracket 166. A power connection 151 supplies power to the coil 137.

Figure 2:
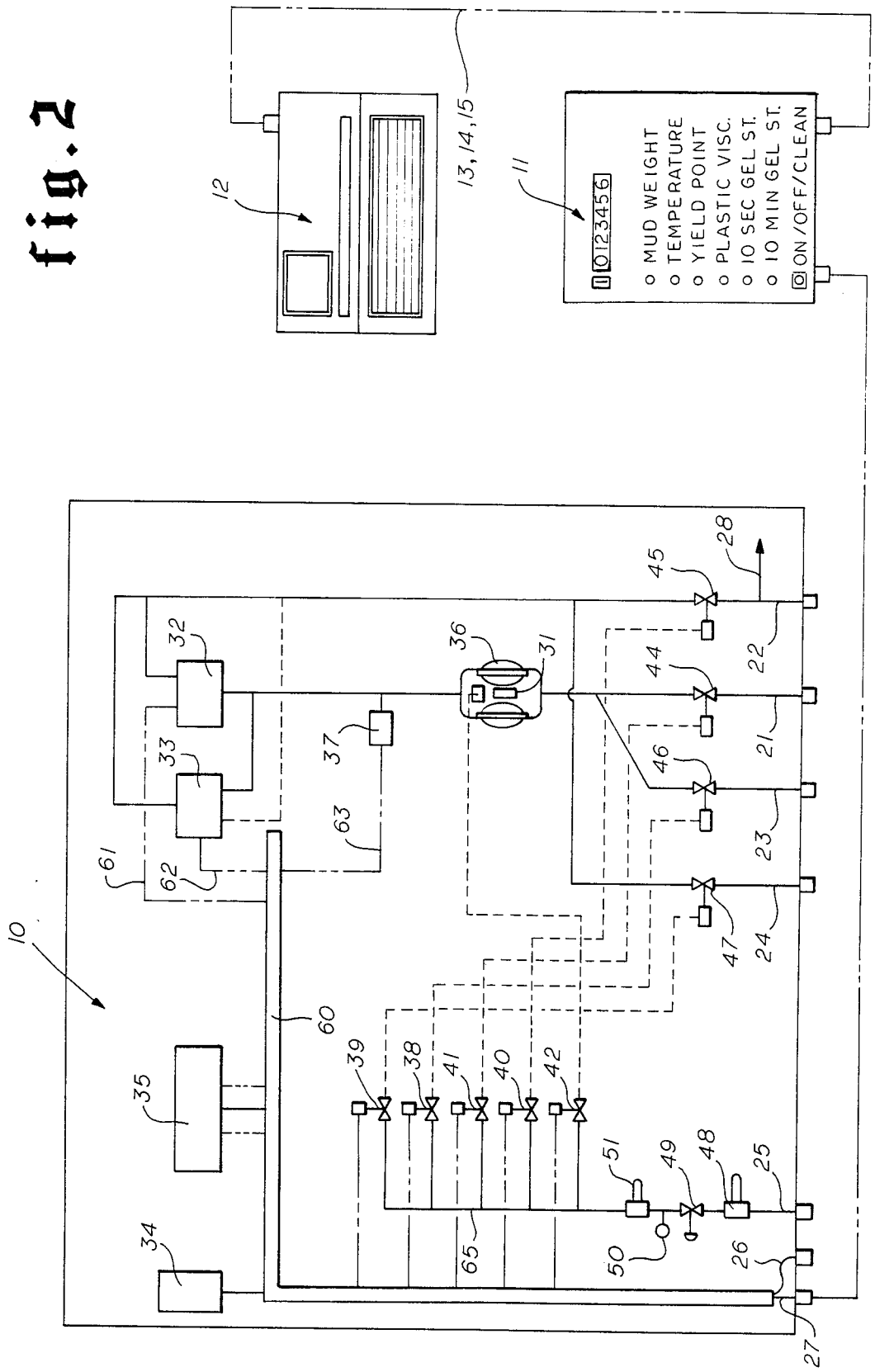
FIG. 2 is a schematic diagram of the system of the present invention, according to a preferred embodiment.
Figure 3:
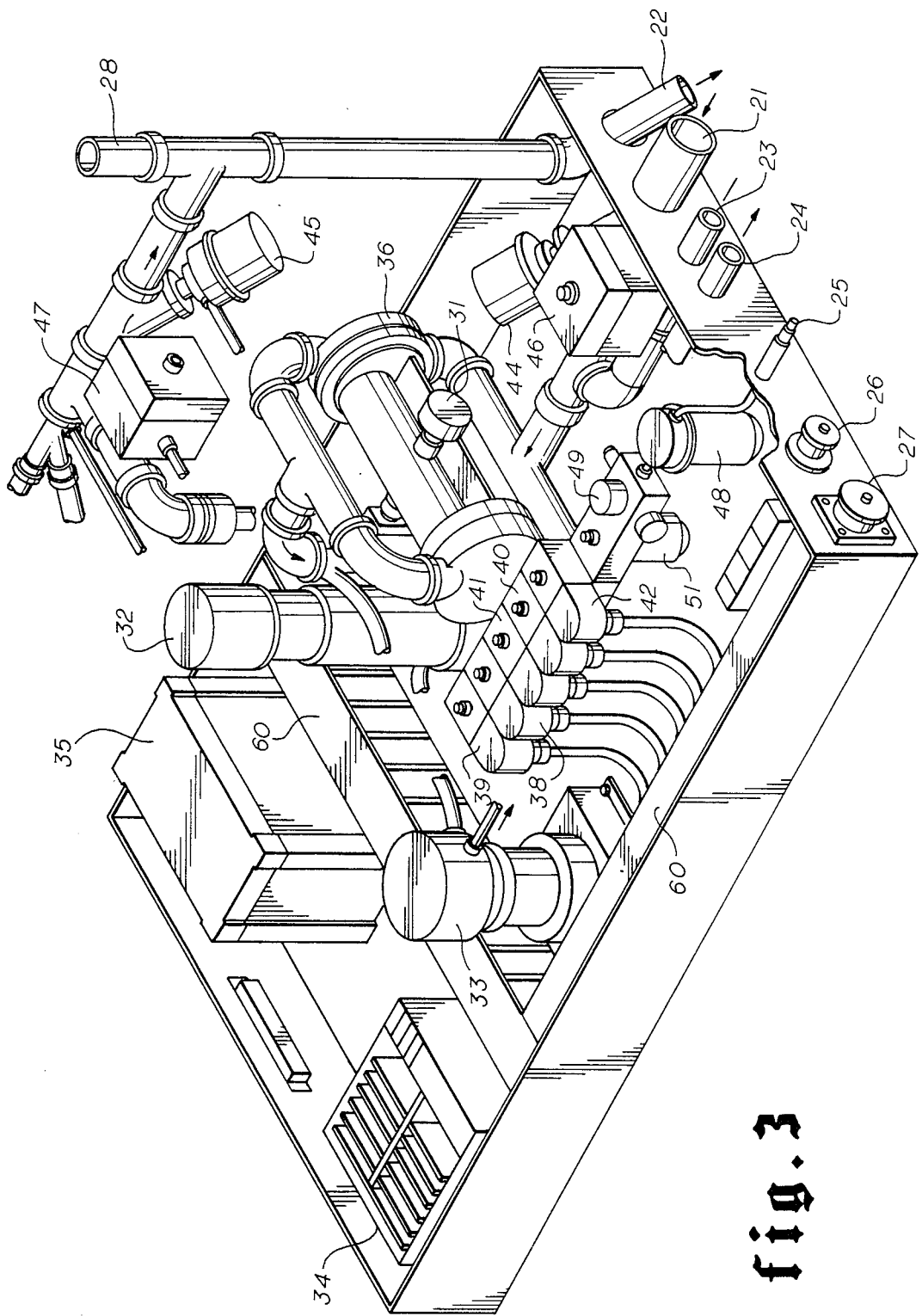
FIG. 3 is a perspective view of the pit transducer, one of the major components of the system of the present invention, according to a preferred embodiment.

The coil 137 is connected through the power connection 151 and 165 to the power center 34 of the pit transducer shown in FIGS. 2 and 3. When power is applied to the coil 137, a force is produced directly proportional to the current, tending to force the coil and the bushing 150 and the pull shaft 168 in an upward direction. The upward force produced by the coil 137 is thus transmitted to the shaft 110 and is sufficient to lift the shaft 110, plate assemblies 111, 112 and any fluids in the chamber 113. The nuts 120 and 125 provide upward and downward stops for this movement.

Figure 5:
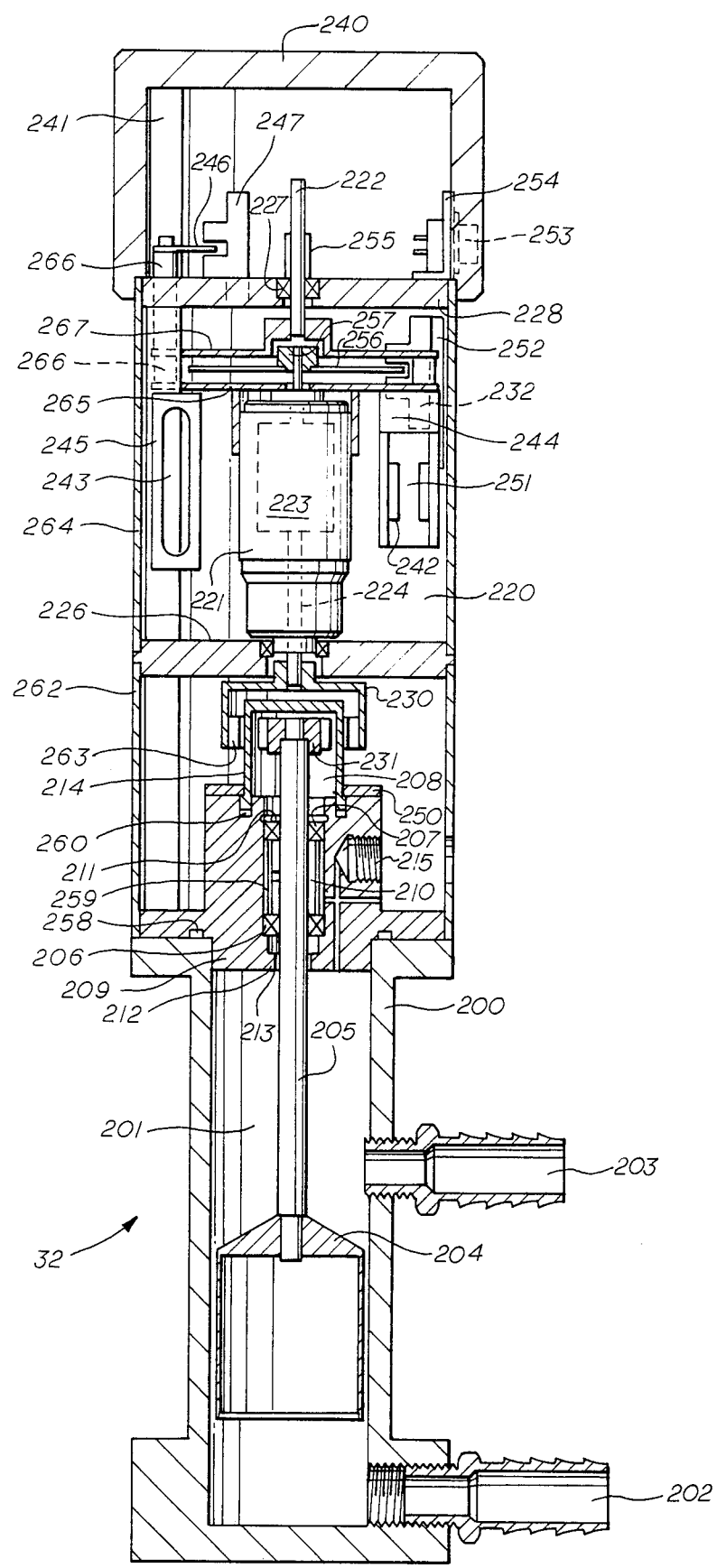
FIG. 5 is a sectional elevational view of a viscosity measuring device, according to a preferred embodiment of the invention.

The design of the viscosity measuring device of the present invention is also unique. It will now be described in more detail with reference to FIG. 5. The viscosity measuring device or viscometer 32 comprises a lower cylindrical housing 200 in which is a fixed volume cylindrical fluid chamber 201 having an inlet 202 through which fluids may be received and an outlet 203 through which fluids may be discharged. Centrally disposed in the fluid chamber 201 is a cylindrical bob 204 which depends from a bob shaft 205. The bob shaft 205 is supported for rotation by two sets of axially spaced bearings 206 and 207 centrally disposed in a bearing support hub 209 which is in turn surrounded by intermediate housing 262. Seal ring 258 seals this connection. Associated with the bearings 206 and 207 are bearing spacers 210, 259 and bearing retainer ring 211. The upper end of the bob shaft 205 extends into a central cavity 208.

It will be noted that the central cavity 208 and bearings 206 and 207 are separated from the lower fluid chamber 201 by inwardly projecting annular wall 212 which is provided with a central aperture 213 through which the bob shaft 205 may pass. The central cavity 208 is closed at the upper end thereof by a plastic cap 214, pressure plate 250 and seal ring 260. A conduit 215 provides a means for introducing air into chamber 201 and cavity 208. Thus, slight air pressure may be maintained in the cavity 208 to prevent fluid in the chamber 201 from affecting the bearings 206 and 207 or entering the cavity 208.

Mounted in an intermediate cavity 220 of an intermediate cylindrical housing 264 is a DC motor having a stator 221 and rotor 223. The stator 221 is attached by a stator mounting bracket 265. Extending upwardly from the stator 221 is a stator shaft 267. Depending downwardly from the rotor 223 is a rotor shaft 224. The motor may be supported in a bearing 225 mounted on an inwardly projecting radial support member 226. The stator shaft 222 may be supported for axial alignment by aligning sleeve 255 and bearings 227 supported by a radial support member or ring 228.

The DC motor is connected to the bob 204 for rotation thereof by a magnetic coupling which includes a female coupling half 230 with magnet 263 attached to the lower end of the rotor shaft 224 and a male coupling half 231 attached to the bob shaft 205. The plastic cap 214 separates the female and male members 230 and 231 of the magnetic coupling. However, since it is a non-magnetic medium, it has no effect on the magnetic coupling. The magnetic coupling provides a positive engagement, non-friction coupling between the DC motor and the bob 204.

Disposed in the cavity 220 of the intermediate housing 264 ia a permanent magnet device 242 creating a constant, permanent magnetic field in the annular space 243. Attached to the stator mounting bracket 265 is a coil bracket 244 on which is carried a coil 245 for concentric disposition within the annular space 243 and under the influence of the permanent magnetic field 251 created by the permanent magnet 242. The coil 245 is connected to an electrical power source from the power center 34 (see FIG. 2) of the system and is capable of producing a force directly proportional to the current applied thereto for creating a torque on the stator 221 in opposition to the torque normally applied to the stator 221 by the operation of the DC motor of which it is a part. The purpose of the coil 245 is to keep the stator 221 at a fixed angular position relative to the cylindrical housings 200, 264. To do this, an optical device 247 is attached to a support ring 228 in the upper cavity 241 enclosed by housing cap 240 to sense the rotational or angular position of the stator 221 by sensing the position of radial vane 246 attached to a vane mounting bracket 266. The optical device 247 is capable of producing an electronic signal which is directed to the control components of the system which in turn causes current in the coil 245 to be increased or decreased so as to maintain a zero angular position of the coil 245 and the stator 221 relative to the cylindrical housings 200, 264. Electrical power may be provided through connection 253 attached by bracket 254.

Attached to the rotor 223 of the DC motor by a mounting hub 257 is a rotation indicator plate 256. Rotation of the indicator plate is sensed by a revolution counter 232 attached to the housing 264 by mounting bracket 252. This measures the speed of the rotor shaft 224 and bob shaft 205 for transmission to the logic and control components of the system.

Thus, the DC motor of the viscometer 32 may be used to drive the bob 204 through a magnetic coupling. With fluid in the chamber 201, it is necessary to overcome sheer stress of the fluid between the outer wall of the bob 204 and the inner wall of the chamber 201. The amount of shear stress necessary to do so is reflected in a torque produced in the stator 221 of the DC motor. This torque is then reflected by a countertorque produced by the coil 245 to keep the stator 221 in a fixed angular position. The current in the coil 245 is thus a linear function of the sheer stress of the fluid medium in the chamber 201 and due to the unique mounting of the DC motor and the magnetic coupling does not include any friction losses from the DC motor.

STATEMENT OF OPERATION

Referring now to all the drawings, operation of the system of the present invention will be described. Control of the system resides within the control or logic center 35 which, as earlier explained, includes a timing sequence card constructed of resistance, capacitance circuits rigidly scheduling the time and sequence in which each event in the operation of the system is to begin and end. The timing sequence card emits a signal at the beginning and end of each event which in turn is electrically conveyed to the appropriate control element.

To begin operation electrical power must be supplied at the power inlet 26 and pressurized air at the air inlet 25. With the power on to the pit transducer 10, the power center 34 is actuated transforming supplied voltage to control voltage and energizing the logic or control center 35, starting the timing sequence card which begins the issuance of initiation signals.

Normally, the first function in the system is the cleaning of all elements of the pit transducer 10. The cleaning cycle begins with simultaneous opening of solenoid valves 42, 39, and 41. This causes power air to be supplied to the fluid pump 36 which upon pulsing attempts to draw suction from either the cleaning medium inlet 23 or the drilling mud inlet 21. Since the solenoid valve 39 is open in the cleaning cycle, suction will be drawn from the cleaning medium inlet 23. Purge air is supplied to the bearing chamber 208 of the viscometer 32 (see FIG. 5). Since the solenoid valve 41 is open, control air is dispatched to the cleaner discharge valve 47 permitting discharge from the system. Thus, the cleaning medium is circulated through the viscosity measuring device 32 and the weight measuring device 33 and the remainder of the system for eventual discharge through the cleaner discharge 24.

As the cleaning cycle is initiated, the motor of the viscometer 32 is energized to spin the bob shaft 205 and bob 204 at 300 rpm. For the next few minutes, the bob 204 may be caused to spin a few seconds, resting a few seconds, and spinning again. Such agitation while cleaning medium is circulating through the device is intended to assist in dislodging any foreign matter which may remain in the measurement chamber 201. After a few minutes, the viscometer drive motor ceases to run for the balance of the cleaning cycle.

The timing sequence card directs that the solenoid valve 41 close, causing the cleaner discharge valve 47 to close. At the same time, solenoid valve 40 is opened permitting control air to flow to the mud discharge valve 45 permitting it to open. This valve 45 remains open for the balance of the cleaning cycle.

A few seconds later the solenoid valve 39 closes interrupting control air to the cleaner inlet valve 46 so that it closes stopping the flow of any fluids to the pump 36. Simultaneously the timing sequence card directs an electrical signal opening a blow-dry air source valve, which permits internal case air suction through an internal vent to the pump 36. For the next few seconds, the balance of the cleaning cycle, the pump draws air suction and circulates the air through the fluid piping, the weight measuring device 33 and the viscosity measuring device 32. The entire cleaning cycle is completed within a few minutes. The cleaning cycle is initiated when the system is first activated. It may also be initiated thereafter on command to purge the system. The housing in which the components of the system are enclosed may be purged with air by NFPA standards or the components may be those designed to be suitable for the environment, i.e. Class 1, Division 1, Groups A,B,C,D, Art. 500, National Electric Code.

Assuming that the system is in operation and a cleaning cycle has just been completed, a sampling cycle will occur as follows. On initiation of the sampling cycle by the timing sequence card the solenoid valves 42, 38 and 40 are directed to be opened. The opening of these valves causes power air to be supplied to the pump 36, control air to be dispatched to mud inlet valve 44 and control air to be dispatched to mud outlet valve 45. With the valves in these positions, drilling mud or fluids are drawn into the pump 36 and circulated through the viscometer 32 and the weight measuring device 33 for eventual discharge at mud discharge 22.

At the beginning of the sampling sequence, the drive motor of the viscometer 32 is energized to spin the bob shaft 205 and the bob 204 at 300 rpm. Thereafter, the bob shaft spins for a few seconds, pauses to rest for a few seconds and spins again. This agitation is intended to cleanse the viscosity measuring chamber 201. During this period of time, the drilling fluid is being circulated through the system components to cleanse the system and equalize temperature of the system components to that of the drilling fluid, finally resulting in the sample of drilling fluid resident in the weight measuring chamber 113 of the weight measuring device 33 and the viscosity measuring chamber 201 of the viscometer 32 in preparation for measurement.

After an initial circulation period, the timing sequence card signals closure of solenoid valves 42 and 38 blocking air supply to the pump 36 and closing the mud inlet valve 44. At this time, the data communication circuit and decoder circuit are open in preparation for measurement of temperature by the temperature indicating device 37. A signal is dispatched to the temperature sensing device 37. The temperature device 37 is preferably a transducer which measures current by consuming a fixed micro-amperage value for each degree Kelvin above K=0. Subtracting output from input indicates the operating temperature and this data is dispatched via the data link interface 27 to annunciator 11 and the computer processor 12.

A few seconds after the temperature is measured, the solenoid valve 40 is closed, causing the mud discharge valve 45 to also be closed. The communication circuit and temperature measurement circuits are also closed. The system remains at rest with samples resident in the weight measuring chamber 113 of the weight measuring device 33 and the viscosity measuring chamber 201 of the viscosity measuring device 32 for a short period of time to permit all fluid movement to cease and to stabilize in the respective chambers. Then the data communication and decoder circuits are opened in preparation for mud weight. The mud in the chamber 113 is weighed in the following manner.

At this point in the cycle, the chamber 113 of the mud weighing device 33 is filled with mud or drilling fluid causing a downward pressure to be exerted on the central shaft 110. The optical device 141, observing the vane 140, observes that the fluid column in chamber 113 is below the "zero" point. The logic center 35 in response thereto dispatches current to the coil 137 to generate force opposing the permanent magnetic field created by the magnets 101 and 138 to elevate the liquid column in the chamber 113 until the optical detector 141 observes that the column has returned to the "zero" point. As previously mentioned, the coil current necessary to accomplish this is a linear function of the weight of the liquid column. This coil current data is then dispatched via the data link interface 27 to the annunciator 11 and computer processor 12 in a signal form indicating the mud weight. Then the mud weight measuring portion of the cycle ceases and the communication and decoder circuits are closed.

Next the system proceeds directly to begin a viscosity measuring sequence. Upon the beginning of the sequence, the drive motor of the viscometer 32 is energized to spin the bob shaft 205 and bob 204 at 600 rpm. Simultaneously, a decoder circuit is opened in preparation for measurement of 600 rpm shear stress data. The application of power to the drive motor is instantaneous permitting rapid acceleration to 600 rpm and its rotation is held precisely at 600 rpm by the electronic revolution counter 232. The bob shaft 205 and bob 204 continue to rotate for a few seconds permitting fluid equilibrium. Then the data communication circuit is opened and measurement of 600 rpm sheer stress accomplished as follows.

The freely mounted drive motor senses a reaction between the bob shaft coupled rotor shaft 224 and the stator shaft 222. The motor regulator card assisted by the optical revolution counter 232 maintains a 600 rpm speed difference between the rotor 223 and the stator 222. As drag occurs on the bob shaft 205, as a result of fluid shear stress, the stator attempts to spin forward to maintain the 600 rpm relative speed differential. The optical device 247 notes this movement through the position of the indicator vane 246. This is signaled to the control center 35 which in turn dispatches current to the coil 245 necessary to return the stator 221 to the zero position. The coil current necessary to return the stator to the zero position, being a linear function of the shear stress of the fluid in the chamber 201, is then measured and transmitted by the communication circuit, after which the communication circuit is again closed.

Next, the timing sequence card provides a signal producing electrical power to the drive motor of the viscometer 32 so as to again spin the bob shaft 205 and bob 204 at 600 rpm for several seconds to agitate the fluid in the chamber 201. The viscometer then rests for ten seconds in preparation for the measurement of the ten-second gel strength. After the ten seconds have lapsed, the communication circuit and the appropriate decoder circuit are opened in preparation for measurement of ten-second gel strength. Simultaneously, the motor regulator printed circuit card begins the gradual application of power to the drive motor to break the gel bond between the bob 204 and the chamber 201. The measurement circuit records the highest level of current encountered prior to bob rotation at 3 rpm. After this measurement is made and recorded, communication and decoder circuits are closed and measurement terminated. Immediately thereafter, the drive motor of the viscometer 32 is driven to spin at 600 rpm for a few seconds to uniformly mix the fluid in the measurement chamber 201. The motor then ceases operation for ten minutes in preparation for a ten-minute gel strength measurement.

After ten minutes of rest, the communication and decoder circuits are activated and the measurement of ten-minute gel strength begun. As in the case of ten-second gel strength measurement, gradual application of power is applied to the motor until the bob rotates at 3 rpm and the maximum value encountered prior to bob rotation is recorded and dispatched as a signal indicating the ten-minute gel strength value.

The sampling cycle thus measures and generates data for indicating the following characteristics of the drilling fluids sampled: temperature, weight, plastic viscosity, yield point, ten-second gel strength and ten-minute gel strength. In addition, the consistency index and flow behavior index for pseudoplastic fluids may be obtained. To do so, the speed of the viscomer may be varied between 0 and 1500 rpm. These values are transmitted to the annunciator 11 and the computer processor 12 for analysis, recall and manipulation thereof. After a sampling cycle is completed the system will automatically continue to alternate between a cleaning cycle and a sampling cycle so that the properties of the drilling fluid are continuously monitored with the readings being taken every few minutes.

Thus, the apparatus and method of the present invention provides real-time measurement of multiple properties of drilling fluids from a single sampling point. This affords a means of extremely accurate monitoring and control of the drilling fluid program for the drilling of a well. The result is a much better controlled well and substantially reduced cost in drilling fluid components. The system of the present invention and the apparatus used therewith is such an advance in the state of the art that most of the prior art methods of doing so should be obsolete.

While single embodiments of the system and apparatus of the invention have been described herein, many variations can be made without departing from the spirit of the invention. Accordingly, it is intended that the scope of the invention be limited only by the claims which follow.

We claim:

1. A system for real-time measurement of multiple properties of drilling fluids from a single sampling point comprising:
    pump means for transferring fluids in said system the suction of which may be alternately communicated through suction conduits with a reservoir of the drilling fluids being measured and a source of cleaning fluids;
    valve means connected in said suction conduits for alternately allowing or preventing fluid communication between said pump means and said drilling fluid reservoir or said source of cleaning fluids;
    weight means connected to the discharge side of said pump means for receiving and measuring the weight of said drilling fluids therefrom;
    viscosity means connected to the discharge side of said pump means for receiving and measuring indices of viscosity of said drilling fluids therefrom;
    power means connected to said pump means, weight means and viscosity means; and
    control means connected to said power means and comprising logic circuitry for operating said pump means, valve means, weight means and viscosity means in predetermined sequences.

2. A system for real-time measurement of multiple properties of drilling fluids as set forth in claim 1 including visual annunciation means remotely connected to said weight means and said viscosity means for visually displaying properties of said drilling fluids measured thereby at a location remote from said drilling fluids reservoir.

3. A system for real-time measurement of multiple properties of drilling fluids as set forth in claim 1 including computer means remotely connected to said weight means and said viscosity means for receiving, recording, retrieving and manipulating signals indicative of the properties of said drilling fluids measured thereby.

4. A system for real-time measurement of multiple properties of drilling fluids as set forth in claim 1 including temperature means connected to the discharge side of said pump means for measuring the temperature of said drilling fluids received by said weight means and said viscosity means.

5. A system for real-time measurement of multiple properties of drilling fluids as set forth in claim 1 in which said power means comprises a source of pressurized air connected to said pump means and said valve means for operation thereof.

6. A system for real-time measurement of multiple properties of drilling fluids as set forth in claim 5 in which said control means comprises electrically operated solenoid valves and logic circuitry for operating said solenoid valves to supply air to said pump means and said valve means in predetermined sequences.

7. A system for real-time measurement of multiple properties of drilling fluids as set forth in claim 1 in which said power means comprises a source of electricity for operating said weight means and said viscosity means, said control means comprising logic circuitry for operating said weight means and said viscosity means in predetermined sequences.

8. A system for real-time measurement of multiple properties of drilling fluids as set forth in claim 1 in which said weight means and said viscosity means, through sequential operation by said power means and said control means, automatically measure the weight, plastic viscosity, yield point, ten-second gel strength and ten-minute gel strength of said drilling fluids.

9. A system for real-time measurement of multiple properties of drilling fluids as set forth in claim 1 in which said power means comprises a source of electrical power and a source of pressurized air, said source of electrical power being connected to said weight means and said viscosity means, said source of pressurized air being connected to said pump means and said valve means through electrically operated solenoid valves, said control means comprising said solenoid valves and logic circuitry for operating said solenoid valves for operation of said pump means and said valve means and for operating said weight means and said viscosity means in predetermined sequences.

10. A system for real-time measurement of multiple properties of drilling fluids as set forth in claim 1 in which said weight means comprises:
    a vertical cylindrical housing;
    upper and lower circular plate means concentrically disposed in said cylindrical housing and vertically spaced from each other to form a constant volume cylindrical chamber defined by said plate means and the inner surfaces of said cylindrical housing, said housing having an inlet through which said drilling fluids may be received in said chamber and an outlet through which said drilling fluids may be discharged from said chamber; and
    lift means adjacent said cylindrical chamber capable of lifting said upper and lower plate means and drilling fluids resident in said chamber therebetween and producing an electrical signal indicative of the weight of said resident drilling fluids.

11. A system for real-time measurement of multiple properties of drilling fluids as set forth in claim 10 including magnetic means adjacent said cylindrical housing producing a constant magnetic field, said lift means including an electrical coil disposed in said magnetic field and capable of producing a force for said lifting of said upper and lower plate means and said drilling fluids resident in said chamber in response to an electrical current applied thereto.

12. A system for real-time measurement of multiple properties of drilling fluids as set forth in claim 11 in which said current is directly proportional to said lifting force providing said electrical signal indicative of the weight of said resident drilling fluids.

13. A system for real-time measurement of multiple properties of drilling fluids as set forth in claim 11 including sensor means supported by said cylindrical housing for sensing the vertical position of said chamber and producing a signal for controlling said electrical current applied to said coil so as to maintain said chamber at a predetermined elevation.

14. A system for real-time measurement of multiple properties of drilling fluids as set forth in claim 13 in which said sensor means comprises a fixed optical device determining the vertical position of said chamber by optically detecting an indicator attached to one of said plate means.

15. A system for real-time measurement of multiple properties of drilling fluids as set forth in claim 13 including limit means associated with said chamber for limiting the vertical movement of said chamber between upper and lower positions.

16. A system for real-time measurement of multiple properties of drilling fluids as set forth in claim 10 in which said upper and lower plate means are mounted on a shaft the axis of which is coincident with the axis of said cylinder.

17. A system for real-time measurement of multiple properties of drilling fluids as set forth in claim 16 in which each of said plate means comprises an upper and lower circular plate member between which is sandwiched a flexible diaphragm, the periphery of said diaphragms being attached to said cylinder, said diaphragms preventing leakage of drilling fluids resident in said chamber but allowing limited vertical movement of said chamber within said housing.

18. A system for real-time measurement of drilling fluids as set forth in claim 16 including sensor means supported by said cylindrical housing for sensing the vertical position of said shaft, said sensor means being capable of producing an electrical signal causing said lift means to lift said upper and lower plate means and said drilling fluids resident in said chamber to a predetermined elevation.

19. A system for real-time measurement of multiple properties of drilling fluids as set forth in claim 1 in which said viscosity means comprises:
 a vertical cylindrical housing at the lower end of which is a cylindrical fluid chamber having an inlet through which said drilling fluids may be received and an outlet through which said drilling fluids may be discharged;
 a cylindrical bob centrally disposed in said fluid chamber depending from a rotatable bob shaft;
 motor means supported by said housing and connected to said bob shaft for rotation of said bob; and
 indicator means responsive to the torque applied to said bob shaft for producing a signal indicative of certain viscosity indices of drilling fluid resident in said fluid chamber.

20. A system for real-time measurement of multiple properties of drilling fluids as set forth in claim 19 in which said motor means comprises a DC motor including a stator and a rotor from which depends a rotor shaft by which said motor means is connected to said bob shaft.

21. A system for real-time measurement of multiple properties of drilling fluids as set forth in claim 20 in which said rotor shaft and said bob shaft are connected by magnetic coupling means.

22. A system for real-time measurement of multiple properties of drilling fluids as set forth in claim 20 including magnetic means supported by said housing to provide a constant magnetic field, said indicator means including coil means disposed in said magnetic field and connected to said power means for producing a force directly proportional to the current applied thereto to counteract the torque applied to said DC motor stator.

23. A system for real-time measurement of multiple properties of drilling fluids as set forth in claim 22 in which said indicator means comprises sensor means near said coil means for sensing the rotational position of said stator and controlling the current applied to said coil means to maintain said stator in a predetermined angular position.

24. A system for real-time measurement of multiple properties of drilling fluids as set forth in claim 23 in which said sensor means comprises a fixed optical device determining the angular position of said stator by optically detecting an indicator attached thereto.

25. A system for real-time measurement of multiple properties of drilling fluids as set forth in claim 20 in which said bob shaft is supported for rotation in bearing means disposed in a cylindrical cavity above said fluid chamber, said fluid chamber and said cavity being separated by a wall through a central aperture of which said bob shaft projects.

26. A system for real-time measurement of multiple properties of drilling fluids as set forth in claim 25 including means for communicating air to said fluid chamber and said cavity for maintaining air pressure therein, preventing fluid in said fluid chamber from entering said cavity through said central aperture.

27. A system for real-time measurement of multiple properties of drilling fluids as set forth in claim 20 including counter means carried by said housing for detecting the rpm of said rotor shaft and producing a control current for maintaining said DC motor at a predetermined constant rpm.

28. A system for real-time measurement of multiple properties of drilling fluids as set forth in claim 27 in which said control means includes means connected to said counter means and said DC motor for rotating said DC motor for preselected periods of time at a plurality of preselected speeds between 0 and 1500 rpm.

29. A system for real-time measurement of multiple properties of drilling fluids as set forth in claim 28 including magnetic means mounted in said housing for producing a force to counteract torque in said DC motor at said preselected speeds and a current associated therewith for producing said signal indicative of said certain viscosity indices of said drilling fluids resident in said fluid chamber.

30. Apparatus for measuring viscosity properties of both Newtonian and non-Newtonian fluids comprising:
 a vertical cylindrical housing at the lower end of which is a cylindrical fluid chamber having an inlet through which fluids may be received therein;

a cylindrical bob centrally disposed in said fluid chamber depending from a rotatable bob shaft;

motor means supported by said housing and connected to said bob shaft by magnetic coupling means for rotation of said bob; and indicator means carried by said housing and responsive to torque applied to said bob shaft for producing signals indicative of certain viscosity indices of fluids resident in said fluid chamber, including yield point, plastic viscosity and gel strength.

31. Viscosity measuring apparatus as set forth in claim 30 including magnetic means mounted in said housing to provide a constant magnetic field, said indicator means including coil means disposed in said magnetic field to produce a force in response to said bob shaft torque by application of a current directly proportional to said torque, said current providing said signal indicative of said certain viscosity indices of said fluid.

32. Viscosity measuring apparatus as set forth in claim 31 in which said indicator means comprises sensor means near said coil means for sensing the rotational position of said coil means relative to the axis of said motor means, and controlling the current applied thereto.

33. Viscosity measuring apparatus as set forth in claim 32 in which said motor means comprises an electrical motor having a stator and a rotor from the rotor of which depends a rotor shaft by which said motor means is connected to said bob shaft.

34. Viscosity measuring apparatus as set forth in claim 33 in which said rotor shaft and said bob shaft are connected by said magnetic coupling means.

35. Viscosity measuring apparatus as set forth in claim 34 in which said coil is attached to said stator.

36. Viscosity measuring apparatus as set forth in claim 35 in which said sensor means comprises an optical device attached to said housing for optically sensing a radial vane attached to said coil means and providing a signal representative of the radial position of said vane relative to the axis of said motor means for said controlling of the current applied to said coil means.

37. Viscosity measuring apparatus as set forth in claim 34 in which the upper end of said bob shaft and at least a portion of said magnetic coupling means is disposed in a cylindrical cavity above said fluid chamber and separated therefrom by a wall through a central aperture of which said bob shaft projects.

38. Viscosity measuring apparatus as set forth in claim 37 including means for communicating air to said fluid chamber and said cavity for maintaining air pressure therein, preventing fluid in said fluid chamber from entering said cavity through said central aperture.

39. Viscosity measuring apparatus as set forth in claim 33 including counter means carried by said housing for determining the rotational speed of said motor means and producing a signal to control the speed thereof.

40. Viscosity measuring apparatus as set forth in claim 30 in which said motor means comprises a DC motor capable of rotating at a plurality of preselected speeds between 0 and 1500 rpm in response to control means attached thereto.

* * * * *